United States Patent [19]
Eversole et al.

[11] Patent Number: 5,952,192
[45] Date of Patent: Sep. 14, 1999

[54] METHOD OF FLUORESCENT ANALYSIS OF BIOLOGICAL SAMPLE UTILIZING BIEBRICH SCARLET

[75] Inventors: Rob Eversole, Plainwell; Leonard Beuving, Kalamazoo; Charles D. Mackenzie, Eaton Rapids, all of Mich.

[73] Assignee: Western Michigan University, Kalamazoo, Mich.

[21] Appl. No.: 09/003,775

[22] Filed: Jan. 7, 1998

[51] Int. Cl.[6] .................................................. G01N 1/30
[52] U.S. Cl. .................... 435/40.52; 435/960; 436/172
[58] Field of Search ............................... 435/40.52, 960; 436/172

[56] References Cited

FOREIGN PATENT DOCUMENTS 695936   2/1996   European Pat. Off. .

OTHER PUBLICATIONS

A. Novelli, Pathologica (Genoa), vol. 88(3), pp. 188–191, 1996.
R. Cowden et al, Histochemistry, vol. 48(2), pp. 93–100, 1976.
A. Juarranz et al, Histochemistry, vol. 84(4–6), pp. 426–431, 1986.
H. Puchtler et al, Histochemistry, vol. 88(3–6), pp. 243–256, 1988.

*Primary Examiner*—Mary E. Ceperley
*Attorney, Agent, or Firm*—Flynn, Thiel, Boutell & Tanis, P.C.

[57] ABSTRACT

Biebrich scarlet forms complexes with proteins contained in biological samples which have unexpected fluorescent properties. The fluorescent Biebrich scarlet-protein complexes are particularly suitable for study by fluorescent microscopy and other fluorometric detection devices, and is particularly suitable for observation by confocal laser scanning microscopes with single and multi-photon excitation capability.

6 Claims, No Drawings

METHOD OF FLUORESCENT ANALYSIS OF BIOLOGICAL SAMPLE UTILIZING BIEBRICH SCARLET

BACKGROUND OF THE INVENTION

In current medical practice, the detection and analysis of biological cells have become essential in the diagnosis and treatment of many ailments. However, since a typical animal cell has a diameter of from about 10 to 20 microns and is colorless and translucent, analyzing these cells is very difficult. Most untreated cells are about 70% by weight water and are almost invisible in an ordinary light microscope, so that a current method of making these cells visible is to stain them with selected organic dyes.

The use of fluorescent markers or probes to examine cells has become very popular. Fluorescent probes have many advantages over traditional staining dyes. Fluorescent markers do not limit the analysis of microscopy specimens to the interference property of transmitted light and provide point sources of narrow band emission spectra as opposed to the transmission of full spectrum light through the entire thickness of a sample under bright field microscopy. Biological tissue often has a high degree of variability of optical properties, such as refractive index and absorption, and, as such, fluorescent markers often provide better three-dimensional imaging than bright field chromophores and have exceptional clarity for labeled objects near the objective.

If a given fluorophore provides sufficient quantum yield at wave lengths sufficiently distinct from the excitation wave length, a brighter image on a darker field will be produced. This improvement of signal-to-noise ratio can result in better resolution when imaging thick biological specimens and/or tissue sections. Additionally, a new technology for analyzing cell specimens, laser scanning confocal microscopy, requires fluorescent markers. Confocal laser scanning microscopy enables the high resolution optical sectioning of biological specimens. Optical sectioning avoids the structural artifacts and invasive nature of mechanical sectioning and permits the visualization of both living and fixed cells. Additionally, the shallow depth of field of from 0.1 to 0.5 microns of confocal laser scanning microscopes selectively limits the information gathered to a small section of the whole sample. This eliminates the background and scattered fluorescence produced by the rest of the specimen and improves the contrast, clarity and detection of the labelled structures.

OBJECTS OF THE PRESENT INVENTION

It is an object of the present invention to provide a dye to be used in the marking of cells for fluorescent detection which has exemplary spectral properties, chemical properties and specificity.

It is another object of the present invention to provide a dye used in the fluorescent marking of cells which is soluble in water at a neutral pH and is capable of forming covalent bonds with cellular constituents in order to prevent the dye from redistributing during tissue preparation and analysis.

It is a further object of the present invention to provide a photofixing fluorescent marker which is capable of identifying eosinophils and their cytoplasmic granules in tissue.

It is a still further object of the present invention to provide a full affixing fluorescent marker which is capable of allowing the visualization of biological cells and their components by confocal laser scanning microscopy.

SUMMARY OF THE INVENTION

The above and other objects of the present invention are met by using Biebrich scarlet as a fluorophore for marking cells for fluorescent detection. It has been discovered that Biebrich scarlet is capable of forming novel fluorescent complexes with proteins contained in tissue samples and is particularly suitable for the study of eosinophil specific granules in individual cells and tissues. Biebrich scarlet-protein complexes can be studied by confocal laser scanning microscopy techniques, including 2-photon confocal laser scanning microscopy. The use of Biebrich scarlet as a fluorophore enables thicker cell tissue samples to be analyzed due to the superior fluorescent properties of the formed complexes.

DETAILED DESCRIPTION OF THE INVENTION

Biebrich scarlet is a water-soluble deep red, anionic dye having the following formula:

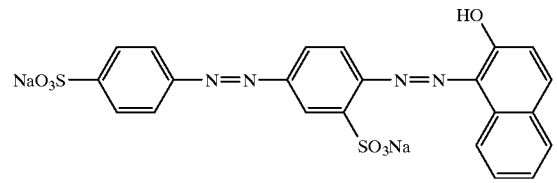

Biebrich scarlet is also known as acid red 66 and is widely available and can be synthesized by well known procedures such as by coupling diazotized 4-amino-1,1'-azobenzene-3, 4'-disulfonic acid to 2-naphthol. Biebrich scarlet is soluble in water and at neutral pHs and, through its sulfonic acid groups, is capable of forming covalent bonds with cellular constituents. The use of Biebrich scarlet as a fluorescent marker is illustrated in the following example.

EXAMPLE

Deparaffinized histological sections having thicknesses of 6 and 60 microns of proximal jejunum from an AUG rat infected with *Nippostrongylus brasiliensis*, nodules excised from the skin of human patients with *Onchocerca volvulus* fixed in 10% neutral buffered formalin and cytocentrifuge preparations of peritoneal lavage, both fixed and unfixed, were prepared. The preparations were rehydrated in distilled water at room temperature for five minutes and then the slides were stained in an aqueous solution of 1% Biebrich scarlet at a pH of 6.8 for 10 seconds for the 6 micron thickness sections and for 10 minutes for the 60 micron thickness sections. The slides were then cleared in running water for 5 minutes, dehydrated in 100% ethanol and washed in xylene before being mounted and allowed to dry over night.

Fluorescent microscopy was performed on the samples using a Nikon FXA epi-fluorescent research microscope with a G-2A filter cassette and the fluorescence intensity measurements were recorded by a Hamamatsu XC-77 CCD camera and analyzed by a Metamorph® Imaging system (a registered trademark of Universal Imaging Corporation).

For confocal laser scanning microscopy, the AUG rat samples were observed by an Ultima-Z-312® (a registered trademark of Meridian Instruments, Inc.) confocal laser scanning microscope with an excitation line at 514 nm and emission filters of 575 nm (short) and 605 nm (long). The human Onchocerca nodules were examined on both Insight Plus® and the Ultima microscope systems (registered trademarks of Meridian Instruments) with an excitation at 488 nm and bandpass filter of 530 nm/30 nm and longpass filter at 605 nm. The images were recorded as TIFF image files on floppy discs and converted to dye sublimation prints on a color digital printer by Tektronix, Inc.

Under the fluorescent microscopy, a deep red fluorescent label was observed in the eosinophil specific granules, red blood cells, some macrophage phagolysosomes and the granules of large granular lymphocytes within the examined tissues. The fluorophore-tissue complexes were the source of emission spectra, greater than 605 nm, upon photoexcitation and proved to be photofixing, producing an increased quantum emission for the first minute of continuous photo-excitation and then stabilizing. All non-specific autofluorescence phenomena associated with these tissues were photobleached in this time frame including areas of background Biebrich scarlet binding wherein photoreactive complexes were not formed, for example, with collagen. The remaining deep red fluorescent emissions were from the various cellular constituents described above in strong contrast to the dark background.

The confocal laser scanning microscopes provided exceptional resolution of individual eosinophil specific granules. Through optical sectioning, the Biebrich scarlet labeled granules were clearly visualized. Additionally, 3-dimensional reconstructions of successive optical sections resolved specific granule profiles and dispersion patterns previously unattainable from whole eosinophil and histological sections. The use of narrow excitation lines in emission filtration showed that the emission spectra varied in wave length from some of the Biebrich scarlet complexes and were distinctly separable.

Although the present invention has been described by way of example to a specific embodiment, the instant invention clearly is not limited thereto and encompasses all modifications and variations thereof that would be obvious to one of ordinary skill in the art.

We claim:

1. In a method of identifying a biological cell in a sample containing the cell wherein the cell is either fixed with formalin or unfixed, combined with a fluorescent marker to form a fluorescent product and the fluorescent product detected with a fluorescence detection device, the improvement comprising combining said cell with a fluorescent marker comprising a dye of the formula

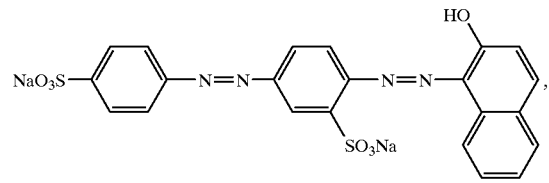

to form the fluorescent product.

2. The method of claim 1, wherein said cell is an eosinophil.

3. The method of claim 1, wherein said sample is human tissue.

4. The method of claim 1, wherein the fluorescent detection device is a fluorescent microscope.

5. The method of claim 1, wherein the fluorescent detection device is a confocal laser scanning microscope.

6. The method of claim 5, wherein the fluorescent detection device is a two-photon confocal laser scanning microscope.

* * * * *